United States Patent [19]

Reed et al.

[11] Patent Number: 5,418,133
[45] Date of Patent: May 23, 1995

[54] SEX DETERMINATION IN CATTLE, SHEEP AND GOATS USING Y-CHROMOSOME POLYNUCLEOTIDES

[75] Inventors: Kenneth C. Reed, Monash; Margaret E. Matthews, Reid; Michael A. S. Jones, Coolah, all of Australia

[73] Assignee: The Australian National University, Australia

[21] Appl. No.: 96,831

[22] Filed: Jul. 26, 1993

Related U.S. Application Data

[63] Continuation of Ser. No. 885,002, May 19, 1992, abandoned, which is a continuation of Ser. No. 633,193, Dec. 31, 1990, abandoned, which is a continuation of Ser. No. 229,860, May 17, 1988, abandoned.

[30] Foreign Application Priority Data

Aug. 12, 1986 [AU] Australia ................. PH7385
Aug. 12, 1986 [AU] Australia ................. PH7386
Aug. 12, 1986 [AU] Australia ................. PH7387

[51] Int. Cl.$^6$ ................. C12Q 1/68; C12P 19/34; C07H 21/04; C12N 15/70
[52] U.S. Cl. ................. 435/6; 435/91.2; 435/320.1; 536/24.31
[58] Field of Search ................. 435/6, 91.2, 320.1; 536/24.31

[56] References Cited

U.S. PATENT DOCUMENTS 4,581,333  4/1986  Kourilaky ................. 435/6
4,769,319  9/1988  Ellis et al. ................. 435/6

OTHER PUBLICATIONS

Lamor et al. Cell 37 pp. 171–177 (1984).
Sylla et al. Gene 29 pp. 343–350 (1984).
Koopman et al., Nature 342:940–942 (1989).
Palmer et al., Nature 342:937–939 1989.
Websters Third New International Dictionary p. 590.
Matthews et al., Cytogene. Cell Genet., vol. 56, pp. 40–41, 1991.

Primary Examiner—Mindy B. Fleisher
Attorney, Agent, or Firm—Bacon & Thomas

[57] ABSTRACT

A nucleic acid isolate capable of hybridizing only to y-chromosome specific DNA sequences of cattle, sheep goats and other ruminants. A method for determining the sex chromosome constitution of a tissue or cell sample using the nucleic acid isolate is also disclosed.

14 Claims, 2 Drawing Sheets

```
         BamHI  10         20         30         40         50
5' - GGATCCGAGA CACAGAACAG GCTGCAATTC CAATACACAG AGGTCATGGT
3' - CCTAGGCTCT GTGTCTTGTC CGACGTTAAG GTTATGTGTC TCCAGTACCA
            60         70         80         90        100
     GGGTGACCCC ACGGCCCTTT GGACGTGCAG CTACAAGGGC TTTCTATCCT
     CCCACTGGGG TGCCGGGAAA CCTGCACGTC GATGTTCCCG AAAGATAGGA
           110        120        130        140        150
     TCTAGAACAG TGGGCTTTCT TTCCCTGTCC TTGCCCTGAG CATGAGCACC
     AGATCTTGTG ACCCGAAAGA AAGGGACAGG AACGGGACTC GTACTCGTGG
           160        170        180        190        200
     CCTTGCCTTT TTTCTGAGGT TTCAGAAATG GACCAGCACT GCAGCATAAG
     GGAACGGAAA AAAGACTCCA AAGTCTTTAC CTGGTCGTGA CGTCGTATTC
           210        220        230        240        250
     CACCTGCTAC CTGCATAGTC TTCCAGTTTG AAAAATCACT CTTTGTACTC
     GTGGACGATC GACGTATCAG AAGGTCAAAC TTTTTAGTGA GAAACATGAG
           260        270        280        290        300
     TTTGAAGAAG GCATATATTC GGAGTAAGGA CTATAGGATG GATGGATTAG
     AAACTTCTTC CGTATATAAG CCTCATTCCT GATATCCTAC CTACCTAATC
           307
     CTTGATC-3'
     GAACTAG-5'
```

FIG. 1

```
         10          20          30          40          50
5' - GGAUCCGAGA  CACAGAACAG  GCUGCAAUUC  CAAUACACAG  AGGUCAUGGU
3' - CCUAGGCUCU  GUGUCUUGUC  CGACGUUAAG  GUUAUGUGUC  UCCAGUACCA
         60          70          80          90         100
     GGGUGACCCC  ACGGCCCUUU  GGACGUGCAG  CUACAAGGGC  UUUCUAUCCU
     CCCACUGGGG  UGCCGGGAAA  CCUGCACGUC  GAUGUUCCCG  AAAGAUAGGA
        110         120         130         140         150
     UCUAGAACAC  UGGGCUUUCU  UUCCCUGUCC  UUGCCCUGAG  CAUGAGCACC
     AGAUCUUGUG  ACCCGAAAGA  AAGGGACAGG  AACGGGACUC  GUACUCGUGG
        160         170         180         190         200
     CCUUGCCUUU  UUUCUGAGGU  UUCAGAAAUG  GACCAGCACU  GCAGCAUAAG
     GGAACGGAAA  AAAGACUCCA  AAGUCUUUAC  CUGGUCGUGA  CGUCGUAUUC
        210         220         230         240         250
     CACCUGCUAC  CUGCAUAGUC  UUCCAGUUUG  AAAAAUCACU  CUUUGUACUC
     GUGGACGAUG  GACGUAUCAG  AAGGUCAAAC  UUUUUAGUGA  GAAACAUGAG
        260         270         280         290         300
     UUUGAAGAAG  GCAUAUAUUC  GGAGUAAGGA  CUAUAGGAUG  GAUGGAUUAG
     AAACUUCUUC  CGUAUAUAAG  CCUCAUUCCU  GAUAUCCUAC  CUACCUAAUC
        307
     CUUGAUC-3'
     GAACUAG-5'
```

FIG. 2

SEX DETERMINATION IN CATTLE, SHEEP AND GOATS USING Y-CHROMOSOME POLYNUCLEOTIDES

This application is a continuation of application Ser. No. 07/885,002, filed on May 9, 1992, now abandoned; which is a continuation of Ser. No. 07/633,193, filed on Dec. 31, 1990, now abandoned which is a continuation of Ser. No. 07/229,860, filed on May 17, 1988, now abandoned.

The present invention relates to sex determination, and is particularly concerned with ruminant sex determination using Y-chromosome specific polynucleotides.

[Note: References cited herein are collected at the end of the specification.]

The capacity to determine the sex of an embryo or a foetus is becoming increasingly advantageous, particularly in light of advances in the area of reproductive biology such as embryo transfer. In the dairy and beef cattle industry alone, some 50,000 embryo transplants were reported to have been carried out in 1985. Given the predisposition of the dairy industry to female progeny, it would be most advantageous if embryos could be routinely sexed prior to transfer into a maternal host. The availability of sexed embryos would allow dairy producers to select replacement progeny for their stock from embryos which possessed desirable traits, such as increased milk production and mothering ability. Similarly, in the sheep and goat industries, the availability of sexed embryos would unable producers to select the most desirable progeny for their stock.

The ability to determine the sex of an embryo or foetus in vitro is also important. In "conventional" pregnancies which do not involve embryo transfer, but rather arise via artificial insemination or natural insemination, the early determination of sex of an embryo or foetus would allow a producer to terminate a pregnancy if an embryo or foetus of the desired sex was not obtained.

The primary sex of a mammal is determined by the presence or absence of the entire Y-chromosome or a functional portion thereof. Gene(s) present on the Y-chromosome are responsible for the formation of the testis, and the development of the male phenotype. The primary sex of an individual mammal is therefore dependent upon whether or not its genome contains certain DNA sequences, specifically those sequences comprising that part of the Y-chromosome which encode gene(s) responsible for testis determination.

The sex or presumptive sex of an individual mammal can therefore be determined by analysis for Y-chromosome specific genes in the DNA of the animal. Alternatively, sex can be determined by analysis for unrelated but genetically linked sequences that are associated specifically with the Y-chromosome. In order to minimise possible errors due to infrequent genetic recombination events, such analyses are best made for sequences which are linked closely to the testis-determining gene(s).

A number of investigators have identified DNA sequences which hybridize preferentially or exclusively to male DNA (1,2). These DNA sequences have not been functionally characterized. Furthermore, it is unknown whether these sequences are capable of hybridization to non-human species.

Australian Patent Application No. 59561/86 discloses bovine DNA probes which hybridize preferentially to male DNA. These DNA sequences are stated to be useful as hybridization probes for sexing in embryos and foetuses.

A particular disadvantage associated with the DNA sequences described in Australian Patent Application No. 59561/86 is that they are species' specific, i.e. bovine specific, and do not hybridize to DNA from other ruminant animals such as sheep or goats. The species specificity of these sequences therefore limits their usefulness as a general reagent for determining the sex of foetuses or embryos of ruminant animals.

The present invention arises from the discovery of a Y-chromosome specific DNA sequence which is universally conserved amongst ruminant animals and has been found in all ruminant animals studied to date. The sequence is repeated to varying degrees, with a repeat number differing between unrelated individuals, and is stabily inheritable.

According to one aspect of the present invention there is provided a nucleic acid isolate capable of hybridizing only to Y-chromosome specific DNA species of cattle, sheep and goats.

The nucleic acid isolate corresponds to all or part of a DNA sequence found on the Y-chromosome of bovine animals referred to hereinafter as BRY.1.

The BRY.1 DNA sequence is shown in FIG. 1. This sequence comprises 307 nucleotides, the first 237 of which were disclosed in Australian Provisional Patent Application No. PH 07385/86; from which the present application claims priority.

The term "BRY.1" refers to the specific DNA sequence set forth in FIG. 1. This term also includes variants where nucleotides have been substituted, added to or deleted from the sequence shown in FIG. 1; as Long as the variants hybridize specifically with all or part of the sequence given in FIG. 1, and diverge by no more than 25% from that sequence.

These variants may be naturally occurring allelic variants which arise within a population of individuals by virtue of point mutations, deletions or insertions of DNA sequences. Alternatively, these variants may be artificially produced, for example, by site directed mutagenesis, deletion of fragments of DNA using endonucleases or restriction enzymes, or the addition of DNA sequences by ligating portions of DNA together.

The present invention also extends to any contiguous portion of 12 or more nucleotides of BRY.1, hereinafter referred to as "oligonucleotides". Such oligonucleotides may be used as hybridization probes to detect BRY.1, and may be synthetically constructed using commercially available DNA synthesizers such as the Applied Biosystems 380A DNA Synthesizer, using standard methods. Oligonucleotides which comprise less than 12 nucleotides have reduced effectiveness as hybridization probes.

According to a further aspect of the present invention, there is provided a nucleic acid isolate comprising any contiguous portion of 12 or more nucleotides of BRY.1.

The present invention also extends to RNA which corresponds to BRY.1 (the RNA sequence corresponding to FIG. 1 is shown in FIG. 2) and any contiguous portion of 12 or more nucleotides of the RNA sequence of FIG. 2.

According to another aspect of the present invention, there is provided a nucleic acid isolate comprising RNA corresponding to one or both strands of BRY.1 or any contiguous portion of 12 or more nucleotides of BRY.1.

The nucleic acid isolate of the invention may be utilized as a hybridization probe, and may be labelled with radioactive markers such as $^{32}P$, $^{14}C$ $^3H$ $^{125}I$ or with non-radioactive markers such as biotin, or bromodeoxyuridine, by known methods (3 to 8).

RNA corresponding to all or part of BRY.1 may be produced using in vitro transcription systems, utilizing for example SP6 RNA polymerase or T7 RNA polymerase (7,8).

The nucleic acid isolate of the present invention may be used as a hybridization probe to detect Y-chromosome specific DNA sequences and hence to determine sex of, for example, an embryo or foetus. Similarly, the nucleic acid isolate may be used to detect variations in amounts and/or minor variations in sequences of BRY.1 in individual animals. Such analysis is useful in paternity testing.

Fractionated sperm may also be tested with a nucleic acid isolate of the present invention. Particularly, sperm enriched for Y-chromosome content can be assessed using the nucleic acid isolate of the present invention.

Where the sex of an embryo, foetus or individual ruminant animal is to be determined, a sample of cells is removed for assay, and DNA is extracted therefrom using known methods (9). The isolated DNA is then bound to a solid support such as nitrocellulose or Zeta-probe membrane (trademark Bio-Rad Corporation) or electrophoresed in a gel matrix and then transferred to a solid support. The solid support is then hybridized with the nucleic acid isolate of the invention which is labelled with a detectable marker as hereinbefore described. Labelled isolate which binds to DNA on the solid support is detected, for example, by autoradiography (10). If the labelled isolate binds to the BRY.1 gene present in the DNA sample, sex can be unequivocally designated male.

In the above method, the target DNA of the embryo, foetus, etc. namely the BRY.1 gene, may be amplified according to the procedures of Saiki et al (11,12).

The nucleic acid isolate of the present invention may also be hybridized to fixed cells or metaphase chromosomes using standard techniques of in situ hybridization (13).

According to a further aspect of the invention, there is provided a method for the determination of the sex chromosome constitution of a tissue or cell sample comprising, isolating DNA from said tissue of cell sample, immobilizing the isolated DNA onto a support matrix, hybridizing the immobilized DNA with a nucleic acid isolate capable of binding only to Y-chromosome specific DNA sequences of ruminants under conditions enabling the nucleic acid isolate to bind to complementary DNA sequences, washing unbound nucleic acid isolate from the support matrix and subsequently detecting binding of said nucleic acid isolate to DNA bound to the support matrix.

According to another aspect of the present invention there is provided a method for determining the presence or absence of a Y-chromosome in fixed cells or metaphase chromosome spreads comprising, hybridizing said fixed cells or metaphase chromosomes with a nucleic acid isolate capable of hybridizing only to Y-chromosome specific DNA sequences of ruminants, under conditions enabling the nucleic acid isolate to bind to complementary DNA sequences, washing away unbound nucleic acid isolate, and detecting binding of the nucleic acid isolate.

According to another aspect of the present invention there is provided a method for determining the sex chromosome constitution of a tissue or cell sample comprising isolating DNA from the tissue or cell sample and denaturing the isolated DNA to separate the respective coding and non-coding strands, annealing the denatured DNA with a synthetic oligonucleotide corresponding to 12 or more nucleotides of the BRY.1, incubating the annealed DNA with DNA polymerase 1 to extend the oligonucleotide through the BRY.1 sequence, if present in the tissue or cell sample; repeating this sequence as many times as desired to amplify levels of BRY.1; and subsequently detecting BRY.1 DNA in the amplified sample either by:

(a) immobilizing the DNA onto a support matrix, hybridizing the immobilized DNA with a nucleic acid isolate capable of hybridizing only to Y-chromosome specific DNA sequences of ruminants which have been labelled with a detectable marker, under conditions enabling the labelled nucleic acid isolate to bind to complementary sequences, washing unbound isolate from the support matrix, and subsequently detecting binding of the nucleic acid isolate to DNA bound to the support matrix; or (b) where labelled nucleotide precursors are included in the incubation with the DNA polymerase, fractionating the sample by electrophoresis in a gel matrix, and detecting labelled BRY.1 sequences which are fractionated in the gel matrix.

Nucleic acid hybridizations are carried out under standard conditions according to the methods of Reed and Mann. (14) and Maniatis et al. (9)

The nucleic acid isolate of the present invention may comprise or form part of a kit for detecting the presence or absence of Y-chromosome specific sequences in a tissue or cell sample. The nucleic acid isolate may be labelled with detectable markers. Kits may include buffers for diluting reagents, labelled compound(s), and solid supports on which assays may be performed.

According to still a further aspect of the present invention, there is provided a method for the isolation of Y-chromosome specific DNA comprising:

(i) annealing single stranded bovine genomic DNA prepared from male and female animals;

(ii) isolating the annealed DNA and inserting it into a replicable vector;

(iii) transforming host cells with the replicable vector containing the annealed DNA; and (iv) hybridizing the transformed host cells with a labelled DNA probe prepared from female ruminant genomic DNA, and identifying those host cells which contain bovine genomic DNA which do not bind with the labelled probe.

DESCRIPTION OF THE DRAWINGS

FIG. 1 shows the double stranded DNA sequence of BRY.1; and in this figure, C refers to deoxycytidine-5'-phosphate, G refers to deoxyguanosine-5'-phosphate; A refers to deoxyadenosine-5'-phosphate; and T refers to deoxythymidine-5'-phosphate.

FIG. 2 shows the double-stranded RNA sequence corresponding to the DNA sequence of BRY.1. In this figure, C refers to cytidine-5'-phosphate; G refers to guanosine-5'-phosphate; A refers to adenosine-5'-phosphate; and U refers to uridine-5'-phosphate.

DEFINITIONS AND ABBREVIATIONS

DNA—deoxyribonucleic acid

RNA—ribonucleic acid
cDNA—complementary DNA (enzymically synthesized from a mRNA sequence)
mRNA—messenger RNA
A—Adenine
T—Thymine
G—Guanine
C—Cytosine
U—Uracil
Tris—Tris (hydroxymethyl) aminomethane
EDTA—Ethylenediaminetetracetic acid
SDS—Sodium dodecylsulphate
psi—pounds per square inch
K.MES—potassium morpholinoethane-sulphonate
polynucleotide—single or double-stranded DNA or RNA

EXAMPLES

EXAMPLE 1

Isolation of BRY.1 DNA (14):

Portions of liver from male and female cattle were collected at an abattoir and immediately frozen in liquid nitrogen. Samples (0.8 g) of frozen liver from individual animals were homogenised in 8 ml of HB(0.1M NaCl, 10 mM Tris-HCl (pH 7.5), 1 mM EDTA). To each homogenate was added, with thorough gentle mixing, 2.2 ml of 0.5M EDTA and 1.22 ml of 20% (w/v) Sarcosyl. The suspensions were heated at 65° C. for 15 min with occasional gentle mixing, 11.6 g of solid CsCl was dissolved in each, then 1 ml of ethidium bromide (10 mg/ml) was added and mixed. The suspensions were transferred into 13.5 ml centrifuge tubes which were placed in a Beckman Ti80 rotor and centrifuged in a Beckman L8–80 ultracentrifuge at 45,000 rpm for 60 h at 25° C.

The pink band of concentrated DNA near the middle of the tube was recovered by side puncture (with an 18 g needle affixed to a 1 ml plastic syringe) and transferred to a capped tube. Ethidium bromide was removed by repeated extraction with butanol (previously equilibrated with saturated NaCl solution) and the resultant clear DNA solution was dialysed against $3 \times 2$ liters of TE (10 mM Tris-HCl, pH 8.0, 1 mM EDTA) at 4° C.

Enrichment for Clonable Male-Specific Sequences by Heterologous Hybridization (15):

One mg of DNA isolated from the liver of a cow was sheared randomly to a mean fragment size of approx. 500 bp by repeated ($5\times$) passage through a French Press under a pressure of 20,000 psi, then precipitated by the addition of sodium acetate (pH 5.0) to 0.25M and ethanol to 70% (v/v) followed by chilling at $-20°$ C. overnight. DNA was recovered by centrifugation and the pellet rinsed with 70% (v/v) ethanol and dried briefly in vacuo.

Nine μg of DNA isolated from the liver of a bull was digested to completion with restriction endonuclease Sau3AI under standard conditions, then extracted successively with phenol and ether. It was recovered by the addition of ammonium acetate to 2M and ethanol to 70% (v/v), mixing thoroughly, freezing in liquid nitrogen, thawing briefly, and centrifuging for 15 min at 4° C. The pellet of digested male DNA was then rinsed with 70% (v/v) ethanol and dried briefly in vacuo.

These two prepared DNA samples (1 mg of randomly sheared female bovine genomic DNA and 9 μg of "restricted" male bovine genomic DNA) were combined in 0.1 ml of PE (50 mM sodium phosphate (pH 6.8), 5 mM EDTA) and denatured by heating at 100° C. for 5 min, then transferred immediately to ice/water and mixed with 0.1 ml of 4M ammonium sulphate in PE. This solution was incubated at 68° C. for 24 h to allow reannealing of the DNA to a $C_0t$ value of 1,320 moles.$1^{-1}$.sec representing an equivalent $C_0t$ of 66,000 moles.$1^{-1}$.sec due to the 50-fold acceleration of reannealing by 2M ammonium sulphate ($C_0t$=molar concentration of single-stranded DNA at time zero (nucleotides/liter)$\times$time(sec); actual $C_0t$ values are standardised by reference to the equivalent reannealing rate in 0.12M sodium phosphate, pH 6.8).

Reannealed DNA was separated from single-stranded DNA by passage of the mixture through a column of hydroxyapatite (HAP). The column matrix was prepared by suspending 3 g of hydroxyapatite (Bio-Rad DNA GRADE) in 200 ml of PB (0.12M sodium phosphate, pH 6.8) and boiling gently for 15 min. The slurry was then poured into a water-jacketed glass column onto a bed of $\frac{1}{4}$" boiled sand (to prevent clogging of the retaining sintered glass disc in the base of the column) and allowed to settle. The HAP column was maintained at 60° C. throughout. After the HAP column had been pre-washed with 25 column volumes of PB, the solution of reannealed DNA was diluted to 5 ml with PB and applied to the HAP column. The column was eluted with 5 column volumes of PB, then with 5 column volumes of 0.6M sodium phosphate, pH 6.8. Approx. 95% of total DNA was recovered in the fraction eluted with PB, representing double-stranded (reannealed) DNA. This fraction was dialysed against TE, concentrated by repeated extraction with butanol, then extracted with (water-washed) ether and centrifuged to remove particulate material. DNA was recovered from the solution by precipitation with sodium acetate/ethanol as described above.

Preparation of Cloning Vector (plasmid pUC9) (16):

The cloning vector was prepared by digestion of 100 μg of plasmid pUC9 with restriction endonuclease BamHI, followed by the addition of SDS to 0.5% (w/v) and 1/6 volume of 1M Tris-HCl, pH 9.0, and incubation at 37° C. for 1 h with 40 μg of calf intestinal alkaline phosphatase (Boehringer ELISA grade). This solution was treated with phenol and DNA recovered by sodium acetate/ethanol precipitation as described above. The restricted DNA was dissolved in TE/0.2% (w/v) Sarcosyl and layered onto a cold (4° C.) linear gradient of 2–25% (w/w) sucrose dissolved in TE/0.2% (w/v) Sarcosyl in a Beckman SW41 ultracentrifuge tube. The tube was centrifuged in a Beckman L8-80 ultracentrifuge at 36,000 rpm for 20 h at 4° C., then fractions of 0.5 ml were collected using a gradient fractionator (ISCO).

Samples (10 μl) of each fraction were electrophoresed in a 1.5% (w/v) agarose gel containing ethidium bromide (0.5 μg/ml) then photographed under ultraviolet illumination (302 nm) to allow visual identification of fractions containing linearised plasmid.

Preparation of Competent Cells:

Competent bacterial cells (Escherichia coli strain JM83) were prepared (17) by first inoculating 100 ml of 2YT medium (sterile 1.6% (w/v) Bacto-tryptone, 1% (w/v) yeast extract, 0.5% (w/v) NaCl, pH 7.4) with JM83 cells and incubating with vigorous shaking until the optical absorbance of the culture at 600 nm was 0.4. The culture flask was chilled in ice/water for 5 min and the cells harvested by centrifugation. The pellet was resuspended in 50 ml of 50 mM $CaCl_2$, allowed to stand on ice for 20 min, then recentrifuged. The pellet was resuspended in 5 ml of cold 50 mM CaCl$_2$ and allowed to stand on ice for 24 h before being used for transformation assays.

DNA was recovered from 20 µl samples of each gradient fraction above by precipitation with ammonium acetate/ethanol as described above. To these samples was added 50 µl of competent JM83 cells, the suspensions were kept on ice for 30 min, heated at 42° C. for 90 sec, then mixed with 0.1 ml of 2YT medium and incubated at 37° C. for 1 h. Cells were recovered by centrifugation, resuspended in 0.2 ml of 2YT medium, plated on 2YT agar (2YT medium with 1.5% (w/v) agar) containing 50 µg/ml ampicillin and incubated at 37° C. overnight. Counting the number of colonies on each plate allowed identification of gradient fractions containing circular (uncut) plasmid.

Gradient fractions #13-16 (numbering started from top of gradient) containing a majority of linear, phosphatased plasmid and little circular plasmid (estimated from transforming ability) were pooled and the DNA recovered by precipitation with sodium acetate/ethanol as described above.

Preparation of Partial "Library" Enriched for Male-Specific DNA Sequences:

Samples of reannealed genomic DNA (200 µg) and gradient-purified linear vector DNA (10 µg) were combined in 5 ml of ligation buffer (66 mM Tris-HCl, pH 7.5, 6.6 mM MgCl$_2$, 1 mM ATP, 100 µg/ml BSA (bovine serum albumin, Boehringer nuclease-free), 10 mM dithiothreitol, and 50 units of T4 DNA ligase (New England BioLabs)) and incubated overnight at 14° C.

Stocks of JM83 cells were prepared by dilution streaking a sample of cells onto LM agar (sterile 1% (w/v) Bacto-tryptone, 0.5% (w/v) yeast extract, 10 mM NaCl, 10 mM MgSo$_4$, 1.5% (w/v) agar) and incubating overnight at 37° C. A few isolated colonies were inoculated into 20 ml of pre-warmed SOB medium (sterile 2% (w/v) Bacto-tryptone, 0.5% (w/v) yeast extract, 10 mM NaCl, 2.5 mM KCl, 20 mM MgSO$_4$), the culture grown with vigorous aeration to an optical absorbance of 0.5 at 550 nm and diluted with 20 ml of sterile SOB:glycerol (60:40 by volume). Samples (0.1 ml) were transferred to 1.5 ml sealable tubes and chilled on ice for 10 min then frozen in dry ice/ethanol and stored at −70° C.

Competent JM83 cells were prepared from single colonies by first scraping a lump of frozen stock cell suspension onto LM agar, dilution streaking and incubating overnight at 37° C. Ten 2.5 mm (diameter) colonies were each suspended in 1 ml of pre-warmed SOB medium by vortex mixing, the suspensions pooled in 90 ml of pre-warmed SOB medium, and the culture incubated with vigorous aeration at 37° C. until the optical absorbance at 550 nm was 0.5. The culture was transferred to 2×50 ml centrifuge tubes, chilled on ice/water for 15 min, then the cells harvested by centrifugation at 4° C. (2,500 rpm for 12 min). The cell pellet was resuspended in 33 ml of ice-cold TEB (sterile 10 mM K-MES (Sigma), pH 6.3, 100 mM RbCl, 45 mM MgCl$_2$, 10 mM CaCl$_2$, 3 mM hexammine cobalt trichloride (Fluka)) and allowed to stand on ice for 15 min. The suspension was centrifuged at 4° C. (2,500 rpm for 10 min) and the pellet resuspended in 8 ml of ice-cold TFB. To the suspension was added 0.28 ml of DMSO (dimethyl sulphoxide, Merck spectroscopic grade) and the mixture swirled and allowed to stand on ice for 5 min, then 0.28 ml of 2.25M dithiothreitol (Calbiochem; sterile solution in 40 mM potassium acetate, pH 6) was added and the cells again swirled and allowed to stand on ice for a further 10 min. Finally, 0.28 ml of DMSO was added and mixed in gently and cells again allowed to stand on ice for 5 min.

Transformation:

Samples of cells (210 µl) were transferred into 24 chilled polypropylene tubes with 10 µl of ligated DNA and the tube were mixed gently and allowed to stand on ice for 30 min. The tubes were then placed in a 42° C. water bath for 90 sec., transferred to ice/water for 2 min., and 0.8 ml of SOC medium (sterile SOB medium containing 20 mM glucose) added and the suspension incubated at 37° C. for 1 h with gentle shaking. The suspensions in 4 tubes were pooled and the cells spread uniformly onto an 82 mm diameter nitrocellulose filter disc (Schleicher & Schull) by vacuum filtration on a modified Buchner funnel. The disc was placed onto 2YT agar containing ampicillin (50 µg/ml) and incubated at 37° C. overnight. This procedure was repeated for all samples, giving 6 filter platings Approx. 1,500 colonies of transformed cells were evident on each filter following overnight incubation, giving a "library" complexity of approx. 9,000 for the 240 µl of annealed genomic DNA used for transformation (equivalent to a total potential complexity of 187,500 transformants for the 5 ml of ligation mixture). The cells on the six filters were gently suspended in 10 ml of SOB medium containing ampicillin (50 µg/ml), the suspension made 20% (v/v) in glycerol, and 1 ml aliquots dispensed into sealed tubes, frozen in liquid nitrogen and stored at −70° C. as the amplified partial library.

Screening of the Partial Enriched Library for Male-Specific Sequences (19):

Four samples of the amplified partial library, each containing approx. 2,000 transformed cells, were each diluted in 4 ml of 2YT agar/ampicillin at 37° C. Each filter ("master") was then used to prepare a replicate screening filter by placing it, colony surface uppermost, onto a pad of 2 sheets of filter paper (Schleicher & Schull 3 MM) and covering it with a fresh nitrocellulose disc (that had been pre-wetted by placing it onto 2YT agar/ampicillin) followed by 2 sheets of 3 MM filter paper. The "sandwich" was pressed firmly with a smooth, velvet-covered aluminium block and the upper 2 sheets of 3 MM filter paper were then removed. The sandwich of two nitrocellulose discs (master and replica) was "keyed" by piercing it a number of times with a 22 g needle attached to a syringe containing waterproof black ink. The filters were then carefully peeled apart and the master filter returned to its 2YT agar/ampicillin plate for storage at 4° C. The replica filter was placed, colony surface uppermost, onto 2YT agar/ampicillin and incubated at 37° C. for approx. 4-6 h (until colonies had grown to a diameter of approx. 0.5 mm) then transferred to 2YT agar containing chloramphenicol (200 µg/ml) and incubated overnight at 37° C. to arrest cell growth without inhibiting plasmid replication (chloramphenicol amplification of plasmid copy number).

The replica filters were then transferred (colonies uppermost) for 5 min onto a pad of 4 sheets of 3 MM filter paper that had been wetted uniformly with 0.5M NaOH, 1.5M NaCl. Excess liquid was blotted from the filters by transferring them to dry 3 MM filter paper (taking care to maintain them in a horizontal orientation at all times to minimise spreading of plasmid DNA liberated from colonies by alkaline treatment) and the alkaline treatment repeated. The blotted filters were then treated twice successively with 0.5M Tris-HCl (pH 7.5), 1.5M NaCl for 5 min similarly to above. After brief blotting, they were allowed to stand on 3 MM filter paper for 30 min. DNA liberated from colonies was fixed to the neutralised filters by heating them in a vacuum oven at 80° C. for 2 h. Cellular debris was then removed from the filters by washing them in 5×SSC (1×SSC is 0.15M NaCl, 15 mM Na$_3$.citrate), 0.5% SDS at 50° C. for 1 h with continuous gentle shaking.

The washed filters were prehybridized overnight with continuous gentle agitation at 42° C. in hybridization solution (50% (v/v) formamide 5×SSPE (1×SSPE is 0.18M NaCl, 10 mM sodium phosphate (pH 7.7), 1 mM EDTA), 1% (w/v) SDS, 0.5 mg/ml heat-denatured, sheared salmon sperm DNA (Sigma, dissolved at 10 mg/ml in distilled water and autoclaved), 0.5% (w/v) skim milk powder). The prehybridized filters were transferred to fresh hybridization solution containing radioactive probe DNA at 10 ng/ml and incubated at 42° C. overnight with continuous gentle agitation.

Probe Preparation:

The radioactive probe DNA was prepared by pooling equal amounts of DNA isolated from the livers of 6 unrelated cows and labelling a portion of the mixture by nick translation. The sample of mixed DNA (0.2 μg) was pre-incubated with 25 pg/ml DNase I (E. coli deoxyribonuclease I) in a total volume of 40 μl containing 50 mM Tris-HCl 9 pH 7.5), 7.5 mM MgCl$_2$, 5 mM dithiothreitol, 0.1 mg/ml BSA, 20 μM dATP, 20 μM dGTP, 20 μM dTTP, and 100 μCi [α-$^{32}$P]dCTP (Amersham; approx. 3,000 Ci/mmol) at 15° C. for 20 min. During this time a minute sample (approx. 0.2 μl) was removed and applied to the origin mark on a small sheet (approx. 4×8 cm) of PEI-cellulose thin layer chromatography material (Merck). Following the pre-incubation, DNA polymerase I (Boehringer; approx. 5 units) was added and incubation continued at 15° C. for 20 min. The nick translation reaction was stopped by the addition of SDS to 1% (w/v) and EDTA to 20 mM, and a second minute sample removed and applied adjacent to the first on the PEI cellulose sheet. The thin layer chromatogram was developed in 0.75M potassium phosphate, pH 3.5, resulting in a separation of dCTP from DNA. The chromatogram was exposed to a sheet of X-ray film (Fuji RX) for 15 min. Development of the X-ray film allowed visual estimation of the efficiency of incorporation of [α-$^{32}$P]dCTP into DNA. This was subsequently quantitated by scintillation counting of appropriate areas of the chromatogram and found to exceed 95% resulting in mixed female bovine genomic DNA labelled at a specific activity of approx. 10$^9$ dpm [$^{32}$p]/μg. Before its addition to the hybridization solution, the labelled DNA was recovered by precipitation with ammonium acetate/ethanol as described above then dissolved in distilled water and denatured by heating at 100° C. for 5 min.

Following hybridization, the nitrocellulose filters were rinsed briefly in 2×SSC at room temperature then washed in 2×SSC, 0.1% (w/v) SDS at room temperature for 15 min. with moderate agitation, followed by washing in 0.5×SSC, 1% SDS at 68° C. for 15 min., again with moderate agitation. They were finally rinsed briefly at room temperature in 0.5×SSC, blotted dry, wrapped in Gladwrap, and exposed to X-ray film (Fuji RX) with a DuPont Cronex "Lightning Plus" (Trademark) intensifying screen at −70° C. for 3 days.

Autoradiography signals on the developed X-ray film correspond to hybridization of recombinant plasmids in discrete colonies with nick translated female genomic DNA. Such colonies contain DNA sequences that are present in multiple copies in female (and therefore male) genomic DNA, since the probe specific activity was equivalent to approx. 1 dpm/10$^6$ base pairs of genomic DNA. Comparison of the autoradiogram with the original master filters allowed the identification of colonies which gave no hybridization signal; cells in these colonies would contain (i) background (non-recombinant) plasmids; (ii) recombinant plasmids containing sequences present in relatively low copy number in the genomes of both male and female cattle; (iii) recombinant plasmids containing sequences present exclusively in the genome of male cattle. Before undertaking more intensive screening analyses (the last mentioned being the colonies of interest), these "negative" transformants were clonally purified.

Colonies that gave no hybridization signal (approx. 80, or 1% of total) were dilution streaked on 2YT agar/ampicillin and incubated overnight at 37° C. Sterile toothpicks were used to transfer samples of eight isolated colonies from each plate onto replica grid patterns on 2YT agar/ampicillin (secondary master) and nitrocellulose discs on 2YT agar/ampicillin (secondary replica). The master plates were incubated overnight at 37° C. and transferred to 4° C. for storage. The replicas were incubated for approx. 6 h at 37° C. then the filter discs were transferred to 2YT agar/chloramphenicol for overnight incubation at 37° C. The filters were then treated, hybridized, washed and autoradiographed exactly as above.

Where 2 or more of the eight clonally purified transformants derived from a single "negative" colony of the primary screen remained negative on secondary screening, one of the negative secondary clones was analysed for plasmid content. A sterile toothpick was used to transfer a portion of such a colony into 20 μl of lysis buffer (NaOH, EDTA, SDS, glycerol, bromocresol green). The mixture was heated at 65° C. for 30 min. then electrophoresed in a 1% agarose gel in parallel with intact circular plasmids of known size. The gels were stained with ethidium bromide and photographed under ultraviolet illumination to allow visual estimation of the size of plasmids in specific transformants. The gels were then soaked in 2 volumes of 0.25M HCl for 15 min. then subjected to capillary transfer in 0.4M NaOH in which the DNA within the gels is sheared, denatured, transferred and fixed to a sheet of charge-modified nylon membrane (Bio-Rad Zeta-Probe) by "alkaline Southern blotting" (14). The membranes were subsequently neutralised by rinsing briefly in 2×SSC then prehybridized for 4 h at 68° C. in hybridization solution (2×SSPE, 1% (w/v) SDS, 0.5% (w/v) skim milk powder, 10% (w/v) dextran sulphate, 0.5 mg/ml sheared, denatured salmon sperm DNA). They were then transferred to fresh hybridization solution containing radioactive probe (mixed female genomic DNA, prepared as described above) and hybridized overnight at 68° C., after which they were washed and autoradiographed as described above. The developed autoradiogram allowed many potential "negatives" to be eliminated from further consideration.

Recombinant colonies (as evidenced by the size of the plasmid contained within them) that still failed to show hybridization under these conditions of increased sensitivity were used to inoculate 2 ml of 2YT medium/ampicillin for overnight cultures at 37° C. Cells were recovered by centrifugation and plasmid isolated from them by the alkaline/SDS lysis procedure (9).

Samples of individual plasmid mini-preps were then labelled by nick translation and used to probe alkaline Southern blots of "restricted" male and female bovine genomic DNA. Four µg of genomic DNA isolated from the livers of each of 2 unrelated cows and 2 unrelated bulls were digested to completion with restriction endonuclease BamHI and electrophoresed in 1% (w/v) agarose mini-gels (Pharmacia GNA-100). Following staining and photography, the gels were treated with acid, the DNA transferred and fixed to Zeta-Probe membranes, and the membranes were neutralised and prehybridised (all procedures as described above). The membranes (one membrane containing DNA from 2 females and 2 males for each plasmid mini-prep) were transferred to samples of fresh hybridization solution, each containing 10% (w/v) dextran sulphate and a radio-labelled plasmid DNA (20 ng/ml). Samples of plasmid mini-preps (approx. 0.2 µg) were labelled by nick translation to a specific activity of approx. $2 \times 10^8$ dpm[$^{32}$P]/µg plasmid DNA as described above. The membranes were subsequently washed, dried, and autoradiographed as described above.

One of the plasmids was seen to give discrete bands of hybridization with the DNA of both males but neither female. This plasmid (pBRY.1) contained an insert of approx. 300 bp (as determined from electrophoretic analysis of restriction digests of the mini-prep).

EXAMPLE 2

Confirmation of Male-Specificity of Plasmid pBRY.1:

A sample (0.2 µg) of pBRY.1 mini-prep was labelled by nick translation and hybridized to alkaline Southern blots of BamHI-digested genomic DNA isolated from peripheral blood lymphocytes of a number of related male and female cattle.

For this experiment, 50 ml of peripheral blood was obtained (using EDTA as anti-coagulant) from each of a sire and 6 dams he had covered, together with the offspring from these matings. Lymphocyte-enriched cell fractions were recovered from the blood samples by Ficoll-Paque (Pharmacia) centrifugation followed by rapid osmotic shock (to lyse the majority of remaining contaminating red cells) and centrifugation to pellet the lymphocytes. DNA was isolated from the lymphocyte preparations with the procedure described above for liver. Samples of DNA (4 µg) were digested to completion with restriction endonuclease BamHI then subjected to electrophoresis, alkaline Southern blotting hybridization and autoradiography with nick translated pBRY.1 as described above. DNA isolated from the sire and from all his male offspring showed identical bands of hybridization. In contrast, DNA isolated from the dams and from all female offspring showed no evidence of hybridization with pBRY.1.

Dot Blot Hybridization with Liver and Kidney DNA:

Samples of DNA isolated from the liver and kidneys of a number of additional unrelated bulls and cows were used to prepare alkaline dot blots. In this experiment, 8 µg of genomic DNA from each animal was diluted into 1 ml of 0.4M NaOH, 20 mM EDTA and heated at 100° C. for 10 min. One-half of this sample (0.5 ml) was transferred into 0.5 ml of 0.4M NaOH, 20 mM EDTA, and after mixing 0.5 ml of this dilution was again transferred into 0.5 ml of 0.4M NaOH, 20 mM EDTA, and the serial dilution repeated to generate 7 dilutions for each sample. The first, third, fifth and seventh samples (0.5 ml of each, containing respectively 4, 1, 0.25 and 0.0625 µg of DNA) were applied to a sheet of Zeta-Probe membrane using a dot-blot micro-filtration manifold (Bio-Rad). Following vacuum filtration, the sample wells were rinsed with 0.4 ml of 0.4M NaOH and the membrane neutralised and hybridized with nick-translated pBRY.1 as described above. Autoradiography showed that none of the DNA samples from female animals hybridized with the probe, whereas all DNA samples isolated from males showed hybridization. The intensity of the autoradiographic dots varied between males, indicating variation between males in the number of copies of BRY.1 in their genomic DNA (approx. 20-fold variation in intensity was observed, suggesting a 20-fold variation between unrelated

We claim:

1. An isolated nucleic acid sequence comprising one or both strands of the 307 base pair BRY.1 nucleotide sequence of FIG. 1 said sequence being capable of detecting Y-chromosome sequences of cattle, sheep and goats.

2. An isolated nucleic acid sequence according to claim 1 which is comprised of ribonucleotides.

3. An isolated nucleic acid sequence according to claim 1 which is labelled with a detectable marker.

4. An isolated nucleic acid sequence according to claim 3 wherein the detectable marker is $^{32}$P, $^{14}$C, $^3$H, $^{125}$I, biotin or bromodeoxyuride.

5. A replicable vector comprising an isolated nucleic acid sequence according to claim 1.

6. A method for the determination of the sex chromosome constitution of cattle, sheep and goats which comprises isolating DNA from a tissue or cell sample obtained from an individual cattle, sheep or goat: immobilizing said isolated DNA onto a support matrix; contacting said immobilized isolated DNA with a single stranded nucleotide sequence of claim 1 under conditions whereby said single stranded nucleotide sequence of claim 1 selectively hybridizes to the Y chromosome if said chromosome is present in said tissue or cell sample; washing unbound nucleic acids from the support matrix and then detecting the binding of said single stranded nucleic acid to said isolated immobilized DNA whereby binding indicates the presence of Y chromosomes and the absence of binding indicates the absence of Y chromosomes.

7. A method as claimed in claim 6 where the tissue or cell sample is obtained from an embryo, a fetus or from sperm or a fraction of sperm.

8. A method as claimed in claim 6 wherein the isolated nucleic acid sequence is labelled with a detectable marker.

9. A method as claimed in claim 8 wherein the detectable marker is $^{32}$P, $^{14}$C, $^3$H, $^{125}$I, biotin or bromodeoxyuride.

10. A kit for detecting the presence or absence of Y-chromosome specific sequences in a tissue or cell sample, from cattle, sheep or goats comprising an isolated nucleic acid sequence according to claim 1.

11. A kit as claimed in claim 10, additionally containing buffers for the dilution of reagents.

12. An isolated nucleotide sequence capable of detecting Y chromosome sequences of cattle, sheep and goats; said nucleotide sequence having a high degree of homology with respect to the DNA sequence of FIG. 1;

said degree of homology being defined as divergence by no more than 25% of the nucleotide sequences of FIG. 1 whereby said isolated nucleotide sequence having a high degree of homology is capable of selectively hybridizing to the nucleotide sequence of FIG. 1.

13. A method for determining the presence or absence of a Y-chromosome in cattle, sheep and goats which comprises hybridizing fixed cells or metaphase chromosome spreads from, an individual cattle, sheep or goat with the single stranded nucleotide sequence of claim 1 under conditions whereby said single stranded nucleotide sequence of claim 1 selectively hybridizes to the Y-chromosome if said chromosome is present in said fixed cells or metaphase spreads; washing away any unbound nucleic acids and then detecting the binding of said single stranded nucleic acid to said fused cells or metaphase chromosome spreads whereby binding indicates the presence of a Y-chromosome and the absence of binding indicates the absence of a Y-chromosome.

14. A method for detecting the presence of sex chromosome constitution of cattle, sheep and goats which comprises isolating DNA from a tissue or cell sample obtained from an individual cattle, sheep or goat; denaturing the isolated DNA to separate respective coding and no-coding strands; annealing the denatured DNA with a nucleotide sequence according to claim 12; incubating the annealed DNA with DNA polymerase to extend the polynucleotide through the BRY.1 DNA sequence if present in the tissue or cell sample; repeating this sequence as many times as desired to amplify levels of BRY.1 and subsequently detecting BRY.1 DNA sequences in the amplified sample whereby the presence of said BRY.1 DNA sequences indicates the presence of the Y-chromosome and the absence of said BRY.1 DNA sequences indicates the absence of said Y-chromosome.

* * * * *